(12) United States Patent
Sinnott

(10) Patent No.: US 12,616,497 B2
(45) Date of Patent: May 5, 2026

(54) SCALPEL BLADE CONTAINER

(71) Applicant: SMARTSTREAM PTY LTD, Queensland (AU)

(72) Inventor: Michael Sinnott, Queensland (AU)

(73) Assignee: SMARTSTREAM PTY LTD., Queensland (AU)

( * ) Notice: Subject to any disclaimer, the term of this patent is extended or adjusted under 35 U.S.C. 154(b) by 157 days.

(21) Appl. No.: 18/433,916

(22) Filed: Feb. 6, 2024

(65) Prior Publication Data

US 2024/0180587 A1    Jun. 6, 2024

Related U.S. Application Data

(63) Continuation of application No. PCT/AU2022/050854, filed on Aug. 5, 2022.

(30) Foreign Application Priority Data

Aug. 6, 2021  (AU) ................................. 2021212158
Aug. 6, 2021  (AU) ................................. 2021902438

(51) Int. Cl.
    *A61B 17/3217*        (2006.01)
(52) U.S. Cl.
    CPC ................................. *A61B 17/3217* (2013.01)
(58) Field of Classification Search
    CPC ................................................. A61B 17/3217
    See application file for complete search history.

(56) References Cited

U.S. PATENT DOCUMENTS

| | | | | |
|---|---|---|---|---|
| 4,395,807 | A | 8/1983 | Eldridge, Jr. et al. | |
| 5,236,135 | A * | 8/1993 | Wilson ...................... | B09B 3/70 |
| | | | | 241/606 |
| 5,271,500 | A * | 12/1993 | Szacon ................ | A61B 50/362 |
| | | | | 206/366 |
| 5,415,315 | A * | 5/1995 | Ramirez .............. | A61B 50/362 |
| | | | | 220/345.2 |
| 5,545,869 | A * | 8/1996 | Piva .................... | A61M 5/3278 |
| | | | | 219/68 |

(Continued)

FOREIGN PATENT DOCUMENTS

| | | | | |
|---|---|---|---|---|
| CN | 117794473 | A | * | 3/2024 |
| DE | 9403362 | U1 | | 7/1994 |

(Continued)

OTHER PUBLICATIONS

Written Opinion and International Search Report of the International Searching Authority for International Application No. PCT/AU2022/050854 mailed Oct. 19, 2022, 6 pages.

*Primary Examiner* — Omar Flores Sanchez
(74) *Attorney, Agent, or Firm* — Edell, Shapiro & Finnan, LLC

(57)                    ABSTRACT
The invention resides in a scalpel blade container for containing removed scalpel blades. The container has a hollow body having an internal space with a first section in which a scalpel blade remover is able to be positioned and a second section in which removed scalpel blades can be contained. A backflow preventer is provided that separates the first section and the second section and allows removed scalpel blades to pass from the first section to the second section but prevents removed scalpel blades from passing from the second section back into the first section.

25 Claims, 6 Drawing Sheets

(56) References Cited

U.S. PATENT DOCUMENTS

| | | | |
|---|---|---|---|
| 5,947,285 A | 9/1999 | Gaba et al. | |
| 2015/0047170 A1 | 2/2015 | Henry | |
| 2024/0105330 A1* | 3/2024 | Bondarenko | G01F 23/292 |

FOREIGN PATENT DOCUMENTS

| | | | |
|---|---|---|---|
| KR | 102190219 B1 | 12/2020 | |
| WO | 9103984 A1 | 4/1991 | |

* cited by examiner

SCALPEL BLADE CONTAINER

FIELD OF THE INVENTION

This invention relates to a scalpel blade container. In particular, the invention relates to a scalpel blade container associated with a scalpel blade remover and will be described in this context.

BACKGROUND OF THE INVENTION

Scalpels are used throughout the world for a variety of medical and non medical procedures. A scalpel normally includes a scalpel handle that is fitted with a removable scalpel blade. After a scalpel has been used, the scalpel blade must be removed from the scalpel handle, the scalpel handle cleaned and a new scalpel blade placed on the scalpel handle. The scalpel blade is usually supplied sterile and the scalpel handle can be used in either a sterile or non-sterile field. The process of both removing and replacing a scalpel blade on a handle is not without risk. In the past fingers, forceps or needle holders were typically used for this process, and a user can easily cut themselves. This is particularly dangerous when the scalpel blade has been used and is covered in a patient's blood or other bodily fluids. Further once a scalpel blade is removed it can still cause injury to downstream workers such as wards persons, porters and laundry staff if the scalpel blade is not immediately contained.

Scalpel blade removers are commonly used in hospitals and multiple other medical settings and non-medical industries to safely remove scalpel blades from scalpel handles. Such scalpel blade removers may be manually operated, with the user having to perform a particular manoeuvre or sequence of actions to remove the scalpel blade, or automatically operated, wherein the user can more simply insert the scalpel blade into the remover which then removes the blade. Some scalpel blade removers have a scalpel blade container that can capture the removed scalpel blades and enclose them securely and safely to avoid injury. The scalpel container and its contents can then be disposed of safely, for example by a designated sharps waste management company.

Automatic scalpel blade removers may be mechanically operated or powered. Such scalpel blade removers usually comprises a mechanism configured to remove the scalpel blade from the scalpel handle in a single step for the user (e.g. insertion of the blade portion of a scalpel into the remover). They are designed for precise movement that is able to be repeated to ensure the reliable, safe removal of a scalpel blade from a scalpel handle. Any interference of the mechanism of the scalpel blade remover may impair the action of the device and may cause ineffective operation. In a worst-case scenario, jamming of the device will render it ineffective, preventing a scalpel blade from being removed from the scalpel handle. This will also put the user at risk of suffering an injury.

Known scalpel blade removers associated with a container are susceptible to having the removed blades jostled about during delivery, logistics, use, handling, or relocation. This may cause the removed blades to become stuck and obstruct the operation of the mechanism of the scalpel blade remover. A disposed blade may even be able to exit the apparatus, posing a serious injury and contamination risk. When an obstruction to the mechanism occurs, this will generally lead to discarding the scalpel blade remover with the associated scalpel blade container prematurely. Attempting to remove the jammed scalpel blade from the scalpel blade container is both difficult and dangerous, putting the user at risk of injury.

OBJECT OF THE INVENTION

It is an object of the invention to overcome and/or alleviate the abovementioned problems and/or provide the consumer with a useful or commercial choice.

SUMMARY OF THE INVENTION

In one form, although not necessarily the only or broadest form, the invention resides in a scalpel blade container for containing removed scalpel blades, the scalpel blade container comprising:

a hollow body having an internal space;

a first section of the internal space of the hollow body in which an automatically operated scalpel blade remover is able to be positioned;

a second section of the internal space of the hollow body in which removed scalpel blades are able to be contained; and a backflow preventer mounted in the hollow body separating the first section of the internal space of the body and the second section of the internal space of the body;

wherein the backflow preventer allows scalpel blades removed by the automatically operated scalpel blade remover to pass from the first section of the internal space to the second section of the internal space but prevents removed scalpel blades from passing from the second section of the internal space back into the first section of the internal space, and consequently prevents a removed scalpel blade from interfering with the automatically operated scalpel blade remover or escaping the scalpel blade container.

The body can be of any desired shape. Typically, the body is made of at least one plastic material. The plastic material may comprise hospital-grade plastics. Preferably the body is made from Polypropylene and/or Acrylonitrile-butadiene-styrene (ABS).

The shape of the body can be varied depending on use. For example, the external shape of the body may include a handle for carrying the scalpel blade container and may also include a mounting area on a base or side of the body.

The automatically operated scalpel blade remover may include a counter and/or a shut-off mechanism.

The scalpel blade remover may be mounted to the body. The scalpel blade remover may be removably mounted to the body. However, generally, the scalpel blade remover is normally fixed to the body.

Preferably, the scalpel blade remover is located within an upper portion of the internal space of the body. The upper portion of the internal space of the body may also be the first section of the internal space.

A lower portion of the internal space of the body may be used to hold removed scalpel blades. The lower portion of the internal space of the body may also be the second section of the internal space.

The backflow preventer may comprise a backflow partition. The backflow partition may be movable between an open position in which blades can pass through the backflow partition and a closed position in which blades are unable to pass through the backflow partition. The movement of the backflow partition between the open position and the closed position may be dependent on the operation of the scalpel blade remover. Alternatively, the movement of the backflow partition between the open position and the closed position may be dependent on the contact of the removed scalpel blade. The weight of the scalpel blade may cause the scalpel blade to pass through the backflow partition.

Normally the backflow partition is immovable once located within the hollow of the body. The backflow partition may be integrally formed or fitted separately. The backflow partition may be formed from pliable material. However, generally, the backflow partition is made from a rigid material. The backflow partition may be made from different material than that of the body.

The backflow partition may extend between at least two walls of the body. Normally, the backflow partition extends between four walls of the body.

Alternatively, the backflow partition extends between at least one a side wall and a base of the body. Normally the backflow partition extends between three side walls and a base of the body.

Normally the backflow preventer includes one or more openings to allow removed scalpel blades to pass from a first side or first section of the backflow preventer to the second side or second section of the backflow preventer.

The backflow preventer may include an orientation device. The orientation device may orientate a removed scalpel blade in a desired orientation to pass through the one or more openings of the backflow preventer.

The backflow preventer may be in the form of a funnel. That is, the backflow preventer may be in the form of a tube or pipe that includes an opening that is wide at the top and narrow at the bottom. The funnel may be a round, rectangular or square funnel.

Alternatively, the backflow preventer may be in the form of a labyrinth, tortuous path or maze. In such a form a scalpel blade may navigate the labyrinth, tortuous path or maze from the first section to the second section under the force of gravity. The labyrinth, tortuous path or maze is preferably shaped and configured such that the scalpel blade cannot easily enter and/or pass through the labyrinth, tortuous path or maze in reverse.

The backflow preventer may at least partially surround the scalpel blade remover. The backflow preventer may surround the scalpel blade remover.

The backflow preventer of the scalpel container can also assist with positioning and stability of the scalpel blade remover and ancillary parts.

In another form, although not necessarily the only or broadest form, the invention resides in a scalpel blade remover able to be positioned within a scalpel blade removal container, the scalpel blade remover including:

a mechanism to automatically remove a scalpel blade from a scalpel handle of a scalpel; and a backflow preventer attached to the mechanism wherein the backflow preventer is configured to separate an internal space of the removal container into a first section in which the scalpel blade remover is able to be positioned and a second section in which removed scalpel blades are able to be collected and allows removed scalpel blades from the mechanism to pass from a first side of the backflow preventer to a second side of the backflow preventer but preventing removed scalpel blades from passing from the second side of the backflow preventer to the first side of the backflow preventer, and consequently prevents a removed scalpel blade from interfering with the mechanism or scraping the scalpel blade removal container.

The backflow preventer may comprise a backflow partition. The first side of the backflow partition may be a first section of an internal space of a container.

The second side of the backflow partition may be a second section of an internal space of a container.

In yet another form, although not necessarily the only or broadest form, the invention resides in a method of preventing removed scalpel blades from interfering with a mechanism of an automatic scalpel removal device, the method including the steps of:

inserting a scalpel blade of a scalpel into an automatic scalpel blade remover of a scalpel blade container;

removing the scalpel blade from a scalpel handle of the scalpel using a mechanism of the automatic scalpel blade remover; and passing a removed scalpel blade from the mechanism of a scalpel blade remover through a backflow preventer;

wherein the backflow preventer allows removed scalpel blades from the mechanism of the automatic scalpel blade remover to pass from a first side of the backflow preventer to a second side of the backflow preventer but preventing removed scalpel blades from passing from the second side of the backflow preventer to the first side of the backflow preventer, and consequently prevents the removed scalpel blade from interfering with the mechanism of the automatic scalpel removal device or escaping the scalpel blade container.

Further features of the invention will become apparent from the detailed description below.

BRIEF DESCRIPTION OF THE DRAWINGS

Embodiments of the invention will be described, by way of example only, with reference to the accompanying figures in which.

DETAILED DESCRIPTION OF THE PREFERRED EMBODIMENTS

Figures 1, 2, 3, 4, 5, 6, 7:
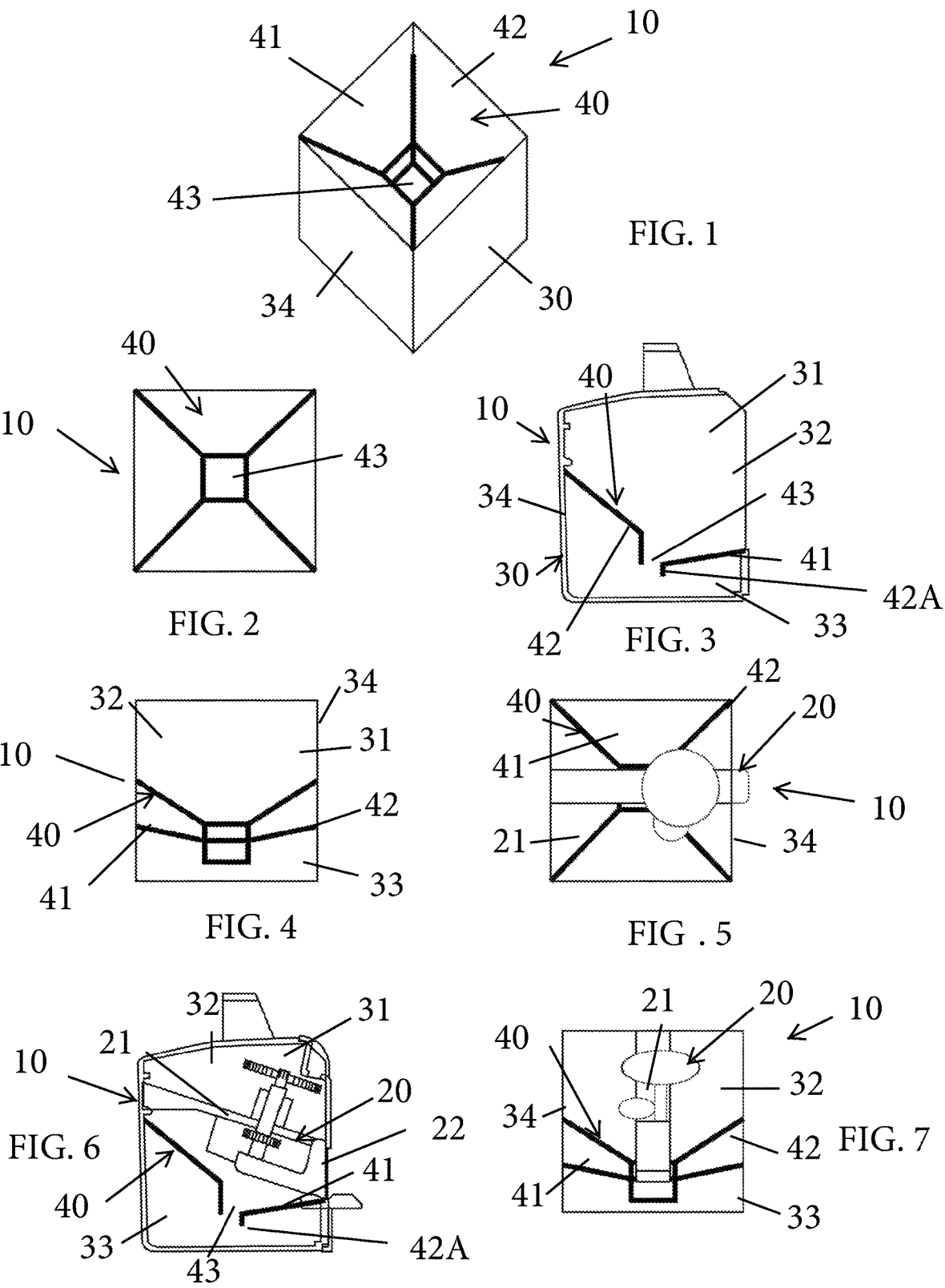
FIG. 1 is a sectional perspective of a scalpel blade container without a scalpel blade remover according to a first embodiment of the invention.
FIG. 2 is a sectional top view of a scalpel blade container without a scalpel blade remover according to FIG. 1.
FIG. 3 is a sectional side view of a scalpel blade container without a scalpel blade remover according to FIG. 1.
FIG. 4 is a sectional front view of a scalpel blade container without a scalpel blade remover according to FIG. 1.
FIG. 5 is a sectional top view of a scalpel blade container according to FIG. 1 including a scalpel blade remover.
FIG. 6 is a sectional side view of a scalpel blade container including a scalpel blade remover according to FIG. 5.
FIG. 7 is a sectional front view of a scalpel blade container including a scalpel blade remover according to FIG. 5.

FIGS. 1 to 7 shows a first embodiment of a scalpel blade container 10 that is used to both remove and contain scalpel blades (not shown) removed from scalpel blade handles (not shown). The scalpel blade container 10 includes a scalpel blade remover 20 (in FIGS. 5 to 7), a body 30 and a backflow preventer in the form of a backflow partition 40.

The scalpel blade remover 20 includes a mechanism 21 that automatically removes scalpel blades from scalpel blade handles. The scalpel blade remover 20 in this embodiment is the same scalpel blade remover 20 disclosed in International Patent Publication No. WO/2013/142897 which is hereby incorporated by reference. However, it would be appreciated by a person skilled in the art that a variety of different scalpel blade removers 20 could be substituted. For example, another scalpel blade remover 20 that could be utilised is disclosed in International Patent Publication No. WO/1996/007363 which is also hereby incorporated by reference.

The body 30 of the scalpel blade container 10 has an internal space 31 that is used both to house the mechanism 21 of the scalpel blade remover 20 and to contain removed scalpel blades. The body 30, in this embodiment, is box-shaped. However, it would be appreciated by a person skilled in the art that the shape of the body may be varied dependent on application. The body 30 is preferably made from hospital grade plastics such as polypropylene and/or polyacrylonitrile-butadiene-styrene (ABS).

The backflow partition 40 divides the internal space 31 of the body 30 of the scalpel blade container 10 into a first section 32, in which the scalpel blade remover is mounted, and a second section 33, in which the removed scalpel blades are contained. It would be appreciated by a person skilled in the art that the size of the first section 32 and the second section 33 may be varied depending on a number of variables including container shape and size, scalpel blade remover size and internal space characteristics.

The backflow partition 40 is used to permit restricted movement of the removed scalpel blades from the scalpel blade remover 20. The backflow partition 40 allows removed scalpel blades to pass from a first section 32 (or a first side) of the backflow partition to second section 33 (or a second side) of the backflow partition 40. However, the backflow partition 40 prevents removed scalpel blades from passing from the second section 33 (or second side) of the backflow partition 40 to the first section 32 (or first side) of the backflow partition 40. Hence the backflow partition 40 prevents scalpel blades from interfering with the operation of mechanism 21 of the scalpel blade remover 20 and/or exiting the container 10.

The backflow partition 40 is formed from a rectangular shaped funnel 41 which is formed from a series of angled walls 42. The series of angled walls 42 define an opening 43 that is wide at its top and narrow at its bottom. The wide top of the opening 43 is located adjacent a base of the scalpel blade remover 20. The top of opening 43 extends the width and breadth of the internal space of the body 30. That is, the funnel 41 is attached to four side walls 34 of body 30.

In use, a scalpel is inserted into the scalpel blade remover 20 through aperture 22. The scalpel blade is removed from the scalpel handle by mechanism 21 of the scalpel blade remover 20 and falls from mechanism 21 of the scalpel blade remover 20. The removed scalpel blade falls into the opening 43 formed by the funnel 41. Walls 42 of the funnel orientate the removed scalpel blade as it travels through the funnel 41 so that when the scalpel blade passes through the narrow end of the opening 43, it passes through the narrow end of opening 43 tip of scalpel blade first.

Once the scalpel blade passes through the funnel 41, it is difficult for the removed scalpel blade to pass back through the funnel 41. This is primarily due to the configuration of the of walls 42 and opening 43 that the blade must pass through in order for the removed scalpel blade to pass back through the funnel 41. When going from the first section 32 to second section 33 the walls 42 of the funnel 41 guide the scalpel blade towards the opening to allow passage therethrough. Once the blade is in the second section 33, however, the walls 42 have the opposite effect, and direct the blade away from the opening 43. Transverse portions 42A of the walls 42 are provided to further inhibit a blade from entering the opening 43 from the second section 33. The transverse portions 42A preferably extend around the perimeter of the opening 43 as illustrated. With such an arrangement the removed scalpel blade must be at a specific location and orientation for the scalpel blade to pass through the narrow opening 43 which is highly unlikely to occur should it try to return to the first section 32 from the second section 33.

Figure 8:
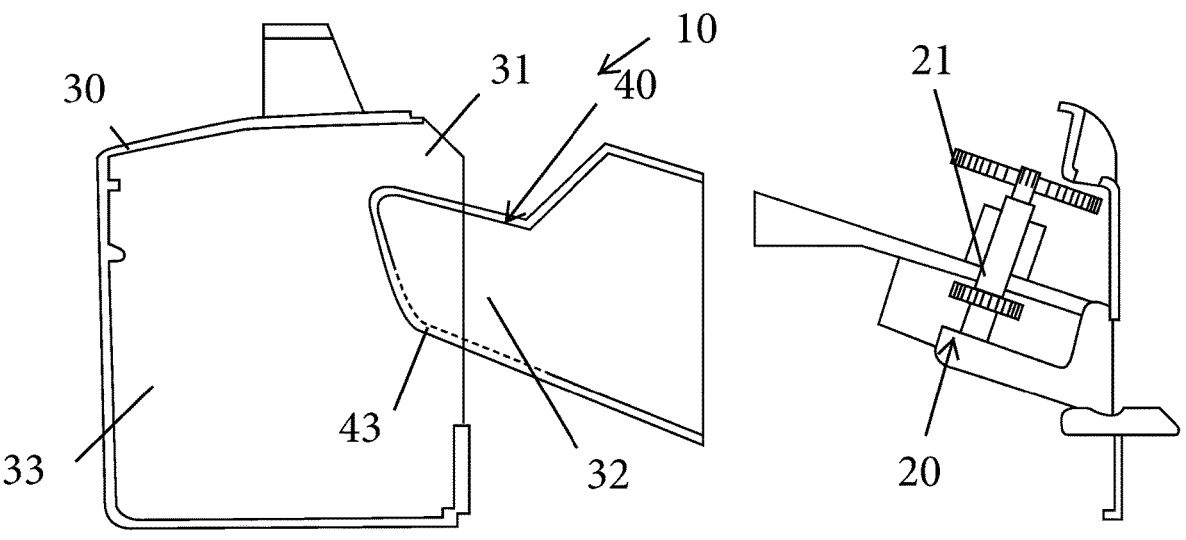
FIG. 8 is a sectional side view of a scalpel blade container including a scalpel blade remover according to a second embodiment of the invention.

FIG. 8 shows a second embodiment of the scalpel blade container 10. In this embodiment, the backflow partition 40 encloses the scalpel blade remover 20. The backflow partition 40 is attached to the scalpel blade remover 20 prior to the backflow partition being located within the body 30. The backflow partition 40 is connected to the body 30 and extends into the internal space 31 of the body 30. The backflow partition 40 divides the internal space 31 into a first section 32 in which the scalpel blade remover 20 is located and a second section 33 in which the removed scalpel blades are caught. An opening 43 extends through the backflow partition 40 adjacent to where a scalpel blade is removed by the mechanism 21 of the scalpel blade remover 20. The backflow partition 40 is rigid, preferably made from a rigid plastic material.

In use, a scalpel is inserted into the scalpel blade remover 20. The scalpel blade is removed from the scalpel handle by the mechanism 21 of the scalpel blade remover 20 and falls from the mechanism 21 of the scalpel blade remover 20. The removed scalpel blade falls from a first side 32 of the backflow partition 40, through the opening 43 in the backflow partition 40, to the second side 33 of the backflow partition being the second section 33 of the internal space 31. The removed scalpel blades fall in a particular orientation and the size of the opening 43 accommodates for this orientation. Accordingly, a removed scalpel blade is unlikely to pass back through the opening 43 and disturb the operation of the scalpel blade remover 20. Similarly, as the backflow partition 40 covers the scalpel blade remover 20, the only way that a removed scalpel blade can alter the operation of the mechanism 21 is via the opening 43 in the backflow partition 40.

Figure 9:
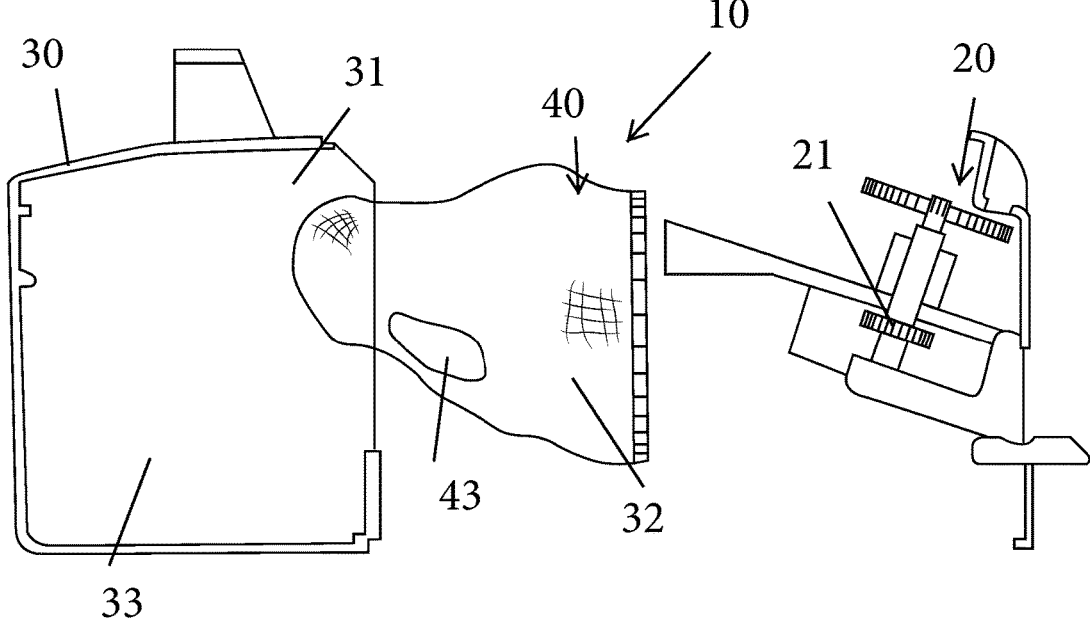
FIG. 9 is a sectional side view of a scalpel blade container including a scalpel blade remover according to a third embodiment of the invention.

FIG. 9 shows a third embodiment of the scalpel blade container 10 that utilises a similar backflow partition 40 to that shown in FIG. 8. In this embodiment, the rigid plastic material of the backflow partition 40 has been replaced with a more flexible material. The use of the backflow partition 40 is the same as described in FIG. 8.

Figures 10, 11:
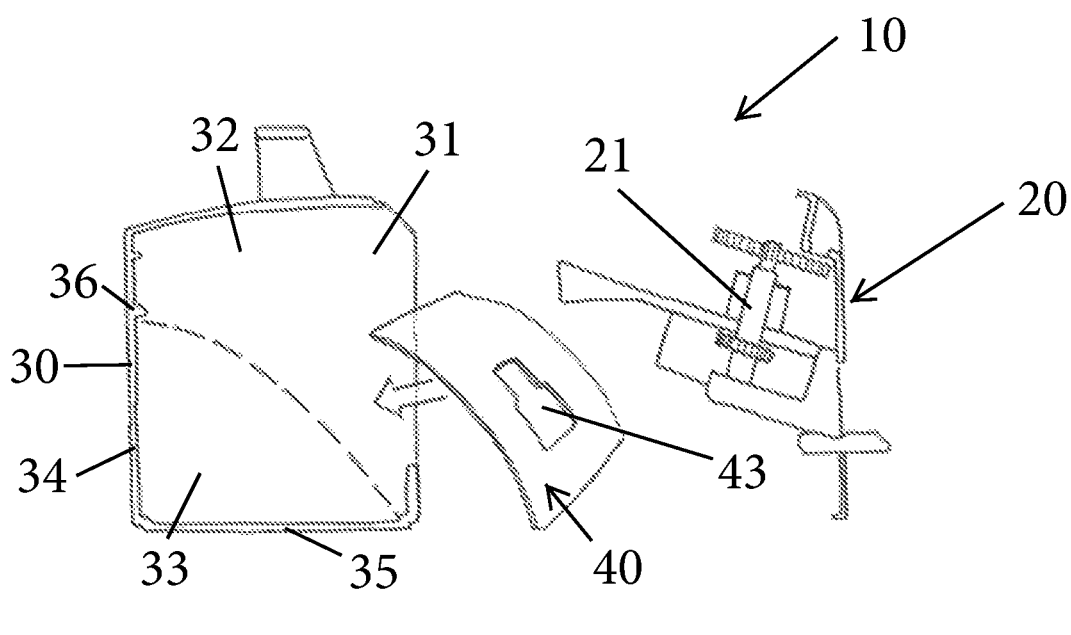
FIG. 10 is a sectional side view of a scalpel blade container including a scalpel blade remover according to a fourth embodiment of the invention.
FIG. 11 is a sectional side view of a scalpel blade container including a scalpel blade remover according to a fifth embodiment of the invention.

FIG. 10 shows a fourth embodiment of the scalpel blade container 10. The backflow partition 40 in this embodiment is located in a similar position to that of the backflow partition described in FIGS. 1 to 7. That is, the backflow partition 40 separates the internal space 31 of the body 30 into a first section 32 where the scalpel blade remover 20 is positioned and a second section 33 to capture removed scalpel blades.

In this embodiment, the backflow partition 40 can be made from a material such as cardboard, thereby reducing the cost of the backflow partition 40. However, it will be appreciated that other suitable materials, such as plastic materials, could be utilised. The backflow partition 40 fixed within the body 30 via tabs 36 with the backflow partition extending between three side walls 34 and base 35 of the body 30. An opening 43 is located within the backflow partition and positioned below the scalpel blade remover 20 so that any removed scalpel blades fall from the first section 32 of the body 30 through the backflow partition 40 into the second section 33 of the body. Similarly, it is difficult for the scalpel blades to pass back through the backflow partition 40 via the opening 43 the sizing of the opening and the required orientation of the removed scalpel blade.

FIG. 11 shows a similar backflow partition 40 to that shown in FIG. 10, with the difference being the material being a mesh as opposed to non-hollow material like cardboard. Further, the backflow partition 40 in this embodiment is differently shaped to enable the insertion of the backflow partition into the internal space 31 of the body 30 in a different manner.

Figure 12:
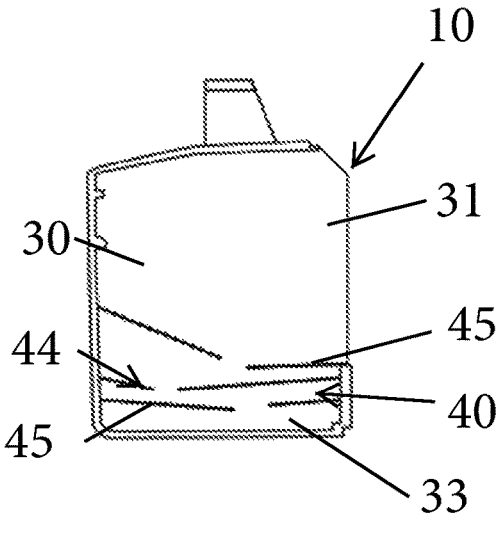
FIG. 12 is a sectional front view of a scalpel blade container without a scalpel blade remover according to a sixth embodiment of the invention.
Figure 13:
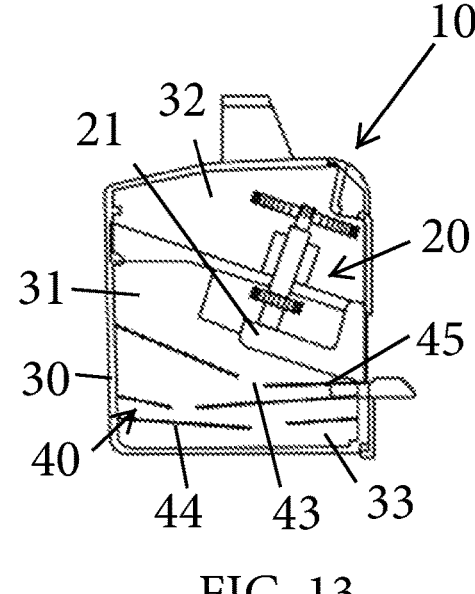
FIG. 13 is a sectional front view of a scalpel blade container according to FIG. 12 with a scalpel blade remover.

FIGS. 12 and 13 show a scalpel blade container 10 that is similar to the scalpel blade container shown in FIGS. 1 to 7 with the scalpel blade remover 20 (shown in FIG. 13) being the same. However, the backflow preventer 40 is different with the rectangular shaped funnel 41 illustrated in FIGS. 1 to 7 being replaced by a maze 44. The maze 44 is formed from a series of screens 45 that extend from the side walls of the body 30 of the scalpel blade container 30. Each of the screens 45 angle downwardly from their respective side wall toward the base of the scalpel blade container. The screens 45 are layered with each alternate screens extending from opposing side walls enabling the screens to overlap. An opening 43 in the form of a tortious path, is formed between the screens 45.

In use, a scalpel is removed from the scalpel handle by the scalpel blade remover 20. The removed scalpel blade contacts a screen 45 and then slides along the screen 45 falling through an opening 43 between the respective screens and on the screen 45 located directly below the opening 45. The scalpel then slides along that screen 45 falling through an opening between the respective screens 45 on the next screen 45 located directly below the opening. This process is repeated until the removed scalpel blade falls from the last opening 45 into the second section 33 of the internal space

31. The scalpel blade is contained here as it is difficult for the scalpel blade to pass back through the maze 44.

Figure 14:
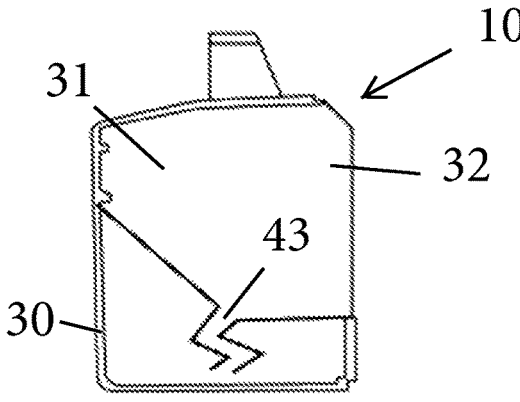
FIG. 14 is a sectional front view of a scalpel blade container without a scalpel blade remover according to a seventh embodiment of the invention.
Figure 15:
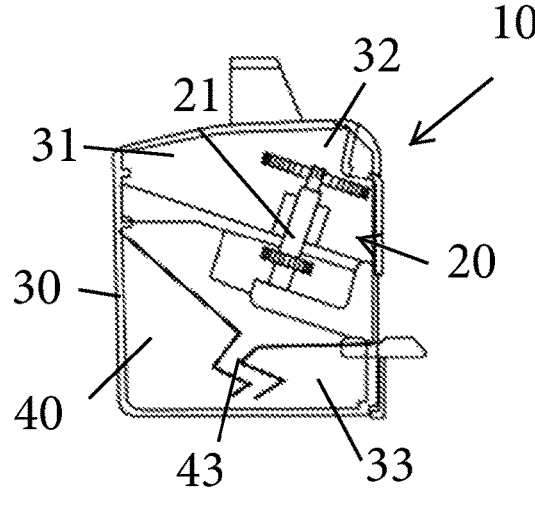
FIG. 15 is a sectional front view of a scalpel blade container according to FIG. 14 with a scalpel blade remover.

FIGS. 14 and 5 show a scalpel blade container 10 that is similar to the scalpel blade container 10 shown in FIGS. 1 to 7 with the scalpel blade remover 20 (shown in FIG. 15) being the same. However, the backflow preventer 40 is different with the opening 43 in the rectangular shaped funnel 41 being replaced by a different shaped opening 43. In this embodiment, the opening is zig-zag shaped when viewed in transverse cross-section. The zig-zag shaped opening 43 allows a removed scalpel blade to pass through the opening in the second section 33 of the internal space 31. However, the shape of the opening decreases the opportunity of a removed scalpel blade form passing back through the opening 43 once it is contained within the second section 33.

Figure 16:
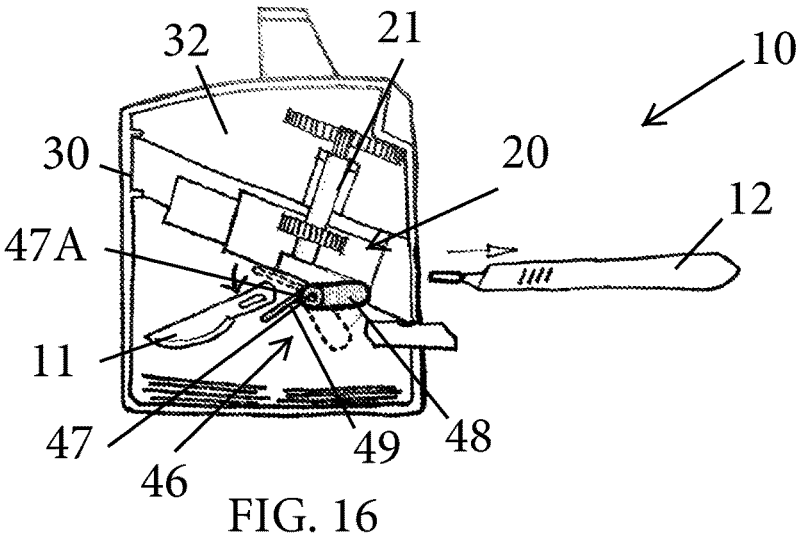
FIG. 16 is a sectional front view of a scalpel blade container with a scalpel blade remover according to an eighth embodiment of the invention.

FIG. 16 shows a scalpel blade container 10 having a backflow preventer in the form of a rocker 46 that is located immediately below the scalpel blade remover 20. The rocker 46 is connected to the scalpel blade remover 20 and is movable between an open and closed position. The rocker 46 includes a pivotal arm 47 which is pivotally mounted through a pivot 47A located immediately below the scalpel blade remover 20. The pivotal arm 47 includes a weighted portion 48 and closure portion 49. The pivotal arm 47 is biased by the weight portion 48 towards the closed position. In the closed position, the closure portion 49 covers the mechanism 21 of the scalpel blade remover 20 and is located immediately below where a removed scalpel blade 11 is ejected from the scalpel blade remover 20. The rocker is sufficiently sized to allow passage of scalpel blades of various lengths and sizes. It should be appreciated that components can be sized to accommodate scalpel blades of varying lengths In use, once the scalpel blade 11 is removed from the scalpel blade handle 12 by the scalpel blade remover 20, the removed scalpel blade contacts the closure portion 49 of the pivotal arm 47. The weight of the scalpel blade causes the pivotal arm 47 to pivot to allow passage of the removed scalpel blade into the second section 33 of the internal space 31. The weighted portion 48 of the pivotal arm 47 then moves the pivotal arm 47 from the open position back to the closed position such that the closure portion 49 covers the mechanism 21 of the scalpel blade remover again.

Figure 17:
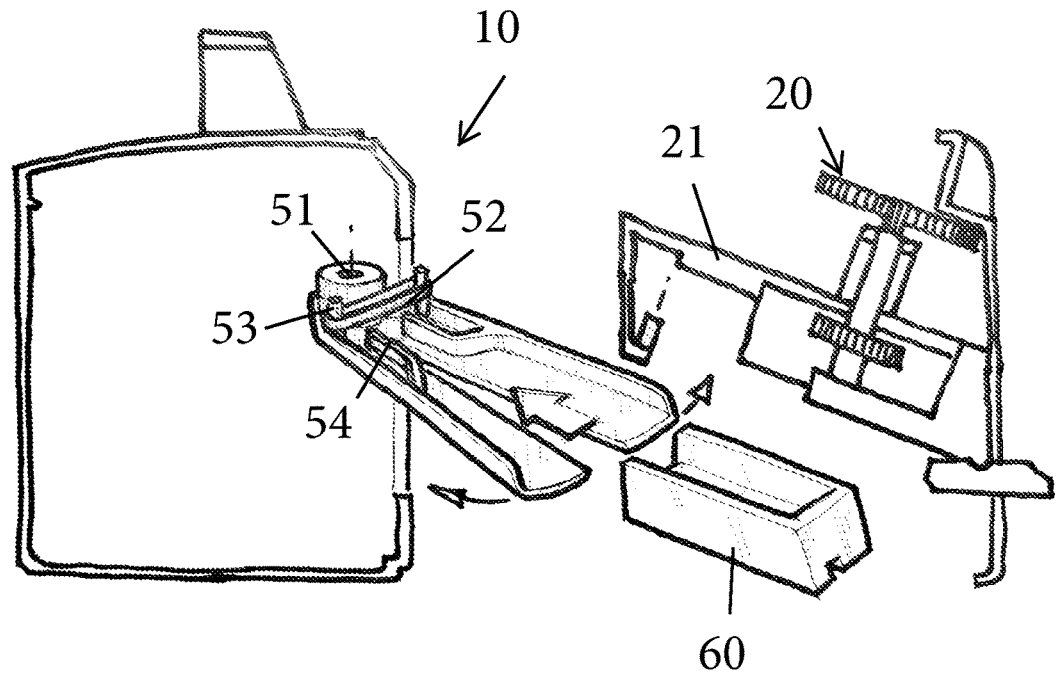
FIG. 17 is an exploded view of a scalpel blade container with a scalpel blade remover according to a ninth embodiment of the invention.
Figure 18:
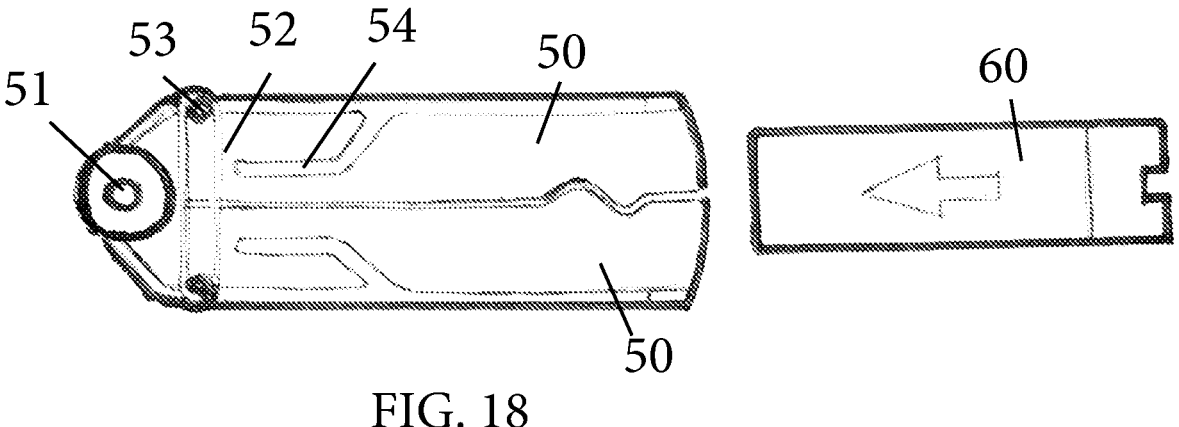
FIG. 18 is a top view of a backflow preventer in a closed position according to a ninth embodiment of the invention.
Figure 19:
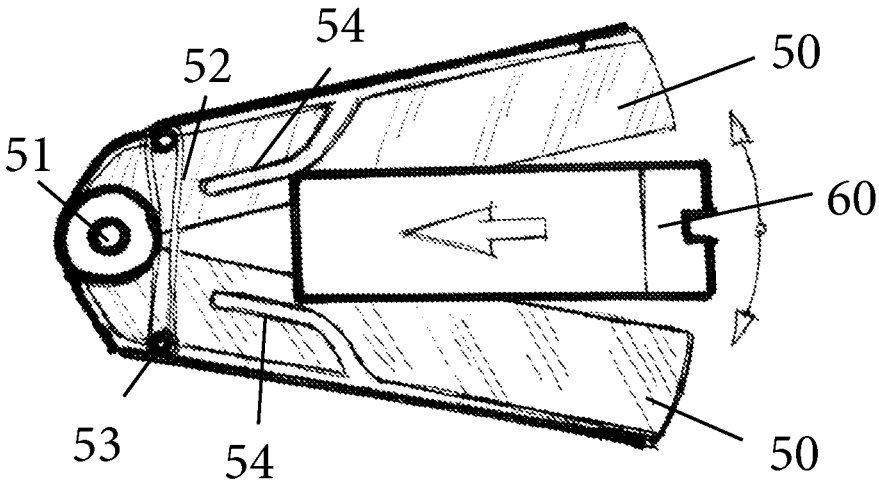
FIG. 19 is a top view of a backflow preventer in an open position according to a ninth embodiment of the invention.

FIGS. 17 to 19 show a further embodiment of a backflow preventer 40. In this embodiment, the backflow preventer 40 is activated by the scalpel blade with handle being inserted into the scalpel blade remover 20. The backflow preventer 40 in this embodiment is located just below the mechanism 21 of the scalpel blade remover 20. The backflow preventer 40 is formed from two jaws 50 that are pivotally connected by a pivot 51. The jaws 50 are movable between an open position and a closed position. A biasing member 52, illustrated in the form of an elastic band, is attached to two attachment teeth 53 located on each jaw 50. The biasing member 52 is used to bias the jaws 50 towards a closed position. A cam 54 is located on each of the jaws 50. It should be appreciated that the biasing member could take other suitable forms such as, for example, a spring.

In use, inserting a scalpel handle 12 with attached scalpel blade 11 drives the slide 60 inwardly so that the slide 60 engages with the cams 54 which spread the jaws 50 apart to an open position. The scalpel blade 11 is then removed by the mechanism 21 of the scalpel blade remover 20 and falls between the opening created by the open jaws 50 into the second section 33 of the internal space 31. As the slide 60 retracts, the biasing member 52 pulls the jaws 50 back together as the slide 60 disengages the cams 54 to move the jaws 50 to a closed position preventing backflow of removed scalpel blades 11.

Advantageously, by having a backflow preventer 40 located within the internal space 31 of a body 30 of a scalpel blade container 10 operational protection of the mechanism 21 of an automatic scalpel blade remover 20 is provided. This reduces the likelihood of user injury through, for example, that user attempting to use a jammed mechanism, and improves the life of the scalpel blade container 10 which reduces unnecessary waste and ensures that users are obtaining value for money. The backflow partition 40 can be readily implemented in a scalpel blade container 10 at minimal cost and with minimal design change.

The backflow preventer 40 also prevents a removed blade scalpel from escaping from the container 10 through the opening that the scalpel was originally inserted. This important safety feature can be provided in a number of different ways, including but not limited to an attached or loose closure device for the opening or by the mechanism used to contain the scalpel blades in the sub-compartment of the scalpel container.

Another function of the backflow feature of the scalpel container is to prevent the removed scalpel blade from interfering with any of the ancillary functions of an automatic scalpel blade remover, such as a counting device and/or a shut-off mechanism.

In this specification, the terms "comprise", "comprises", "comprising" or similar terms are intended to mean a non-exclusive inclusion, such that a system, method or apparatus that comprises a list of elements does not include those elements solely, but may well include other elements not listed.

In this specification, terms such as upward, downward, horizontal and vertical, and their grammatical derivatives, are used to describe the invention in its normal orientation and are not to be construed to limit the invention to any particular orientation.

The reference to any prior art in this specification is not, and should not be taken as, an acknowledgement or any form of suggestion that the prior art forms part of the common general knowledge.

It should be appreciated that various other changes and modifications may be made to the embodiments described without departing from the spirit or scope of the invention.

The invention claimed is:

1. A scalpel blade container for containing removed scalpel blades, the scalpel blade container comprising:
a hollow body having an internal space;
a first section of the internal space of the hollow body in which an automatically operated scalpel blade remover is able to be positioned;
a second section of the internal space of the hollow body in which removed scalpel blades are able to be contained; and
a backflow preventer mounted in the hollow body separating the first section of the internal space of the body and the second section of the internal space of the body;
wherein the backflow preventer allows scalpel blades removed by the automatically operated scalpel blade remover to pass from the first section of the internal space to the second section of the internal space but prevents the removed scalpel blades from passing from the second section of the internal space back into the first section of the internal space and, consequently prevents a removed scalpel blade from interfering with the automatically operated scalpel blade remover, including any ancillary functions of the automatically operated scalpel blade remover including a counting device and/or a shut-off mechanism, or escaping the scalpel blade container.

2. The scalpel blade container of claim 1, wherein the scalpel blade remover is mounted within the first section of the internal space.

3. The scalpel blade container of claim 1, wherein the scalpel blade remover is removably mounted to the body.

4. The scalpel blade container of claim 2, wherein the scalpel blade remover is fixed to the body.

5. The scalpel blade container of claim 2, wherein the scalpel blade remover is located within an upper portion of the internal space of the body, the upper portion of the internal space of the body also being the first section of the internal space.

6. The scalpel blade container of claim 2, wherein the backflow preventer at least partially surrounds the scalpel blade remover.

7. The scalpel blade container of claim 1, wherein a lower portion of the internal space of the body is used to hold the removed scalpel blades, the lower portion of the internal space of the body also being the second section of the internal space.

8. The scalpel blade container of claim 1, wherein the backflow preventer comprises at least one backflow partition.

9. The scalpel blade container of claim 8, wherein the at least one backflow partition is immovable once located within the hollow of the body.

10. The scalpel blade container of claim 8, wherein the at least one backflow partition is integrally formed with the body.

11. The scalpel blade container of claim 8, wherein the at least one backflow partition is fitted separately.

12. The scalpel blade container of claim 1, wherein the backflow preventer is made from different material than that of the body.

13. The scalpel blade container of claim 1, wherein the backflow preventer includes one or more openings to allow the removed scalpel blades to pass from the first section to the second section.

14. The scalpel blade container of claim 13, wherein the backflow preventer includes an orientation device to orientate the removed scalpel blade in a desired orientation to pass through the one or more openings of the backflow preventer.

15. The scalpel blade container of claim 1, wherein the backflow preventer comprises a funnel.

16. The scalpel blade container of claim 1, wherein the backflow preventer comprises a labyrinth, tortuous path or maze.

17. The scalpel blade container of claim 1, wherein the backflow preventer is used to stabilise the scalpel blade remover.

18. A scalpel blade remover able to be positioned within a scalpel blade removal container, the scalpel blade remover including:
a mechanism to automatically remove a scalpel blade from a scalpel handle of a scalpel; and
a backflow preventer attached to the mechanism;
wherein the backflow preventer is configured to separate an internal space of the removal container into a first section in which the scalpel blade remover is able to be positioned and a second section in which removed scalpel blades are able to be collected and allows the removed scalpel blades from the mechanism to pass from a first side of the backflow preventer to a second side of the backflow preventer but prevent the removed scalpel blades from passing from the second side of the backflow preventer to the first side of the backflow preventer, and consequently prevents a removed scalpel blade from interfering with the mechanism, including any ancillary functions such as a counting device and/or a shut-off mechanism, or escaping the scalpel blade removal container.

19. The scalpel blade remover of claim 18, wherein the backflow preventer comprises a partition.

20. The scalpel blade remover of claim 19, wherein a first side of the partition is the first section of the internal space of the removal container and a second side of the partition is the second section of the internal space of the removal container.

21. The scalpel blade remover of claim 19, wherein the partition at least partially surrounds the scalpel blade remover.

22. A method of preventing removed scalpel blades from interfering with a mechanism of an automatic scalpel removal device, the method comprising:

inserting a scalpel blade of a scalpel into an automatic scalpel blade remover of a scalpel blade container;

removing the scalpel blade from a scalpel handle of the scalpel using a mechanism of the automatic scalpel blade remover; and passing a removed scalpel blade from the mechanism of the automatic scalpel blade remover through a backflow preventer;

wherein the backflow preventer allows removed scalpel blades from the mechanism of the automatic scalpel blade remover to pass from a first side of the backflow preventer to a second side of the backflow preventer but prevent the removed scalpel blades from passing from the second side of the backflow preventer to the first side of the backflow preventer, and consequently prevents the removed scalpel blade from interfering with the mechanism of the automatic scalpel blade remover, including any ancillary functions of the automatic scalpel blade remover including a counting device and/or a shut-off mechanism, or escaping the scalpel blade container.

23. The method of claim 22, wherein the backflow preventer comprises a funnel.

24. The method of claim 22, wherein the backflow preventer comprises a labyrinth, tortuous path or maze.

25. The method of claim 22, wherein the backflow preventer comprises a backflow partition.

* * * * *